US012605278B2

(12) United States Patent
Gliner et al.

(10) Patent No.: US 12,605,278 B2
(45) Date of Patent: Apr. 21, 2026

(54) PHACOEMULSIFICATION TIP TYPE DETECTION

(71) Applicant: JOHNSON & JOHNSON SURGICAL VISION, INC., Irvine, CA (US)

(72) Inventors: Vadim Gliner, Haifa (IL); Adam Walter Toner, Ladera Ranch, CA (US); Assaf Govari, Haifa (IL); Andres Claudio Altmann, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 472 days.

(21) Appl. No.: 18/094,547

(22) Filed: Jan. 9, 2023

(65) Prior Publication Data

US 2023/0255821 A1 Aug. 17, 2023

Related U.S. Application Data

(60) Provisional application No. 63/309,756, filed on Feb. 14, 2022.

(51) Int. Cl.
*A61F 9/007* (2006.01)

(52) U.S. Cl.
CPC ................................. *A61F 9/00736* (2013.01)

(58) Field of Classification Search
CPC .................................................... A61F 9/00736
See application file for complete search history.

(56) References Cited

U.S. PATENT DOCUMENTS

| | | | |
|---|---|---|---|
| 5,357,967 A | 10/1994 | Dixon et al. | |
| 5,406,503 A | 4/1995 | Williams, Jr. et al. | |
| 5,425,704 A | 6/1995 | Sakurai et al. | |
| 5,431,664 A | 7/1995 | Ureche et al. | |
| 5,938,677 A | 8/1999 | Boukhny et al. | |
| 7,509,831 B2 | 3/2009 | Khashayar | |
| 7,648,465 B2 | 1/2010 | Gordon | |
| 8,162,919 B2 | 4/2012 | Cull et al. | |
| 8,858,492 B2 | 10/2014 | Fitzgerald et al. | |
| 10,398,595 B2 | 9/2019 | Zacharias | |
| 10,926,022 B2 | 2/2021 | Hickey et al. | |
| 2002/0121135 A1 | 9/2002 | Rediniotis et al. | |
| 2003/0060863 A1 | 3/2003 | Dobak, III | |
| 2009/0018488 A1 | 1/2009 | Davis et al. | |
| 2010/0280439 A1 | 11/2010 | Kuebler | |
| 2012/0072197 A1 | 3/2012 | Ovchinnikov | |
| 2012/0232466 A1 | 9/2012 | Kuebler et al. | |
| 2014/0114237 A1 | 4/2014 | Gordon | |
| 2014/0276897 A1 | 9/2014 | Rockley | |
| 2017/0224888 A1* | 8/2017 | Hickey ............... A61M 3/0208 | |
| 2020/0297375 A1 | 9/2020 | Wang et al. | |
| 2022/0339034 A1 | 10/2022 | Govari et al. | |

(Continued)

FOREIGN PATENT DOCUMENTS

| | | |
|---|---|---|
| EP | 1504724 A1 | 2/2005 |
| EP | 2379126 B1 | 4/2015 |

(Continued)

*Primary Examiner* — Robert J Michaud

(57) ABSTRACT

Systems and methods are provided for detecting the actual tip or tip type being used on a handpiece of an ophthalmic instrument. By detecting the tip type being used, the correct system settings can be used during the surgical procedure, and the surgical system may operate safely.

19 Claims, 6 Drawing Sheets

(56)     References Cited

U.S. PATENT DOCUMENTS

2022/0339341 A1     10/2022  Govari et al.
2023/0000589 A1*    1/2023  Lee ................ A61B 17/320068
2023/0320897 A1     10/2023  Hajishah et al.

FOREIGN PATENT DOCUMENTS

EP          2848218  B1      1/2017
GB          2506883  A       4/2014

* cited by examiner

IRRIGATION LINE

ASPIRATION LINE

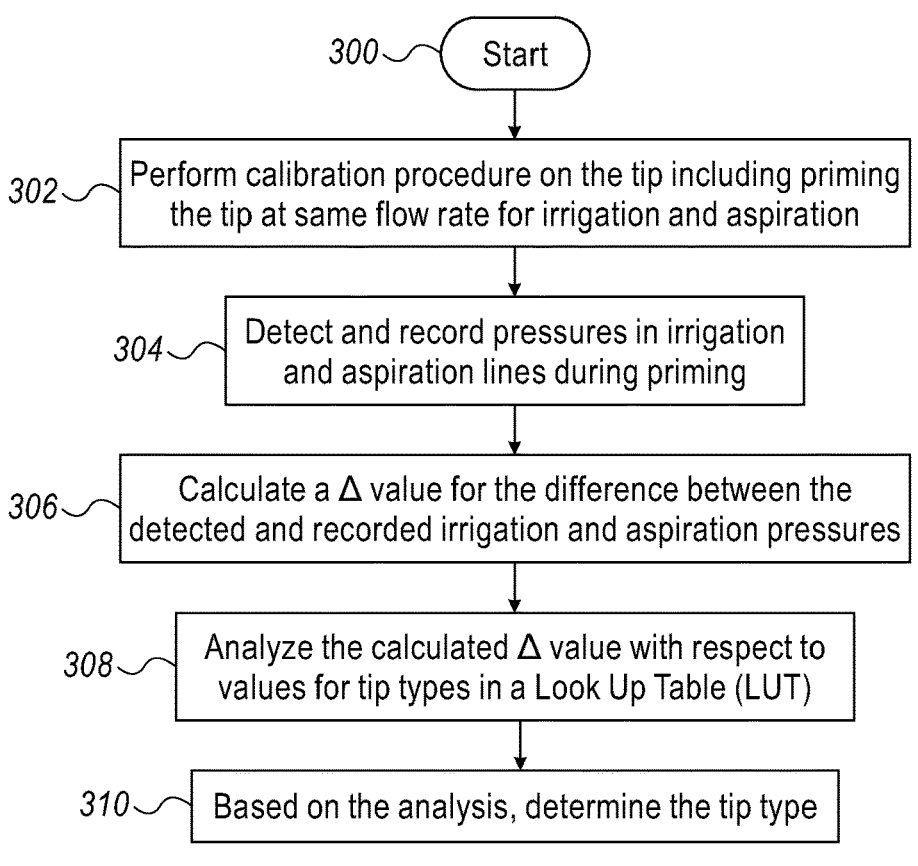

*300* ○ Start

*302* Perform calibration procedure on the tip including priming the tip at same flow rate for irrigation and aspiration

*304* Detect and record pressures in irrigation and aspiration lines during priming

*306* Calculate a Δ value for the difference between the detected and recorded irrigation and aspiration pressures

*308* Analyze the calculated Δ value with respect to values for tip types in a Look Up Table (LUT)

*310* Based on the analysis, determine the tip type

*FIG. 4A*

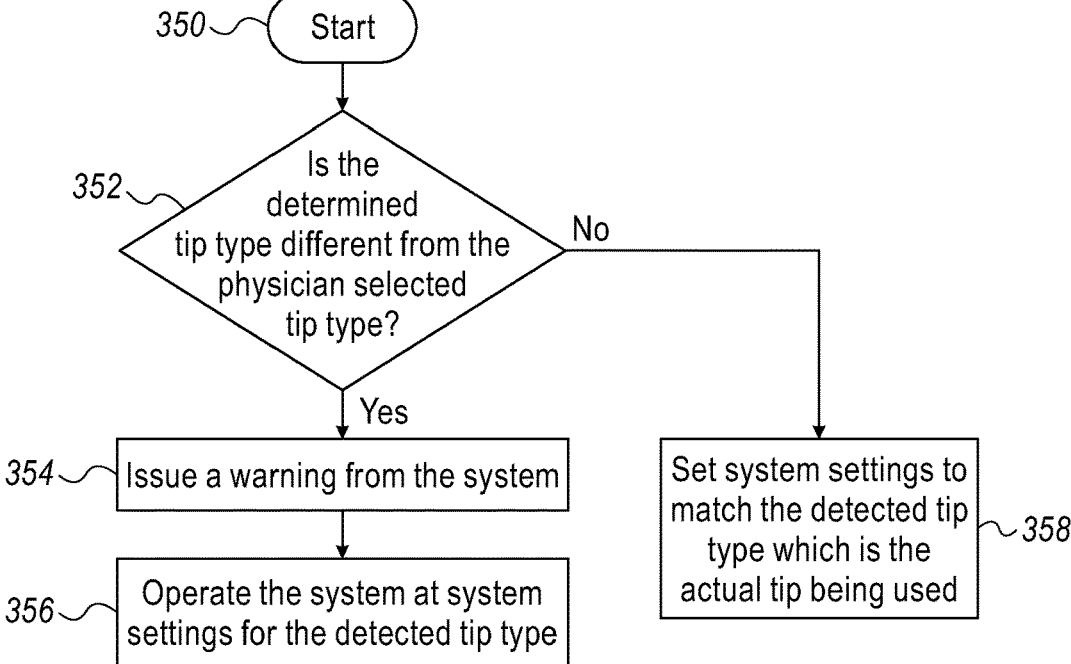

*350* ○ Start

*352* Is the determined tip type different from the physician selected tip type?

No

Yes

*354* Issue a warning from the system

*356* Operate the system at system settings for the detected tip type

*358* Set system settings to match the detected tip type which is the actual tip being used

*FIG. 4B*

PHACOEMULSIFICATION TIP TYPE DETECTION

CROSS-REFERENCE TO RELATED APPLICATIONS

This application claims the benefit of U.S. Provisional Patent Application 63/309,756, filed Feb. 14, 2022, whose disclosure is incorporated herein by reference.

TECHNICAL FIELD

The present disclosure relates generally to natural lens removal device handpieces, and particularly to methods and systems for detecting the tip being used on a handpiece.

BACKGROUND OF THE DISCLOSURE

Ophthalmic surgical apparatuses, such as those used in phacoemulsification procedures, typically include operating controls for regulating settings or functions of the apparatus. Numerous types of apparatuses include as part of the apparatus, a hand-held medical implement or tool, such as a handpiece with a tip. Operation of the tool requires control of various operating settings or functions based on the type of tool used. Such apparatuses typically include a control module, power supply, an irrigation source, one or more aspiration pumps, as well as associated electronic hardware for operating a multifunction handheld surgical tool in order to sonically emulsify eye tissue, irrigate the eye with a saline solution, and aspirate the emulsified lens from the eye.

Different tip types are used in phacoemulsification procedures. Each tip is different in both needle and sleeve diameter. The pressure offset and maximal flow that can be achieved depends on the tip being used.

BRIEF DESCRIPTION OF THE DRAWINGS

The present disclosure will be more fully understood from the following detailed description of the examples thereof, taken together with the drawings in which:

FIG. 4A is a flow diagram of an example process for determining tip type with detected pressure measurements from aspiration and irrigation lines of the system of FIG. 1;

FIG. 4B is a flow diagram for an example process for verifying the tip type with the disclosed system;

DETAILED DESCRIPTION OF EXAMPLES

Overview

When performing ophthalmic surgical procedures, such as phacoemulsification procedures, the physician may be required to identify the type of tip being used with the handpiece. If there is a mismatch between the actual tip being used with the handpiece, and system settings for a different tip, the system may attempt to operate at a working range that is not suitable for the actual tip being used. This may be a safety hazard. In addition, the physician may replace the tip during a procedure. When replacing a tip, the physician is required to prime and/or record the replacement. Sometimes the physician may neglect to do this.

The present disclosure provides systems and methods for detecting the actual tip or tip type being used on the handpiece. By detecting the actual tip type for the tip actually being used, the system settings being used are correct, and the surgical system operates safely.

System Description

Figure 1:
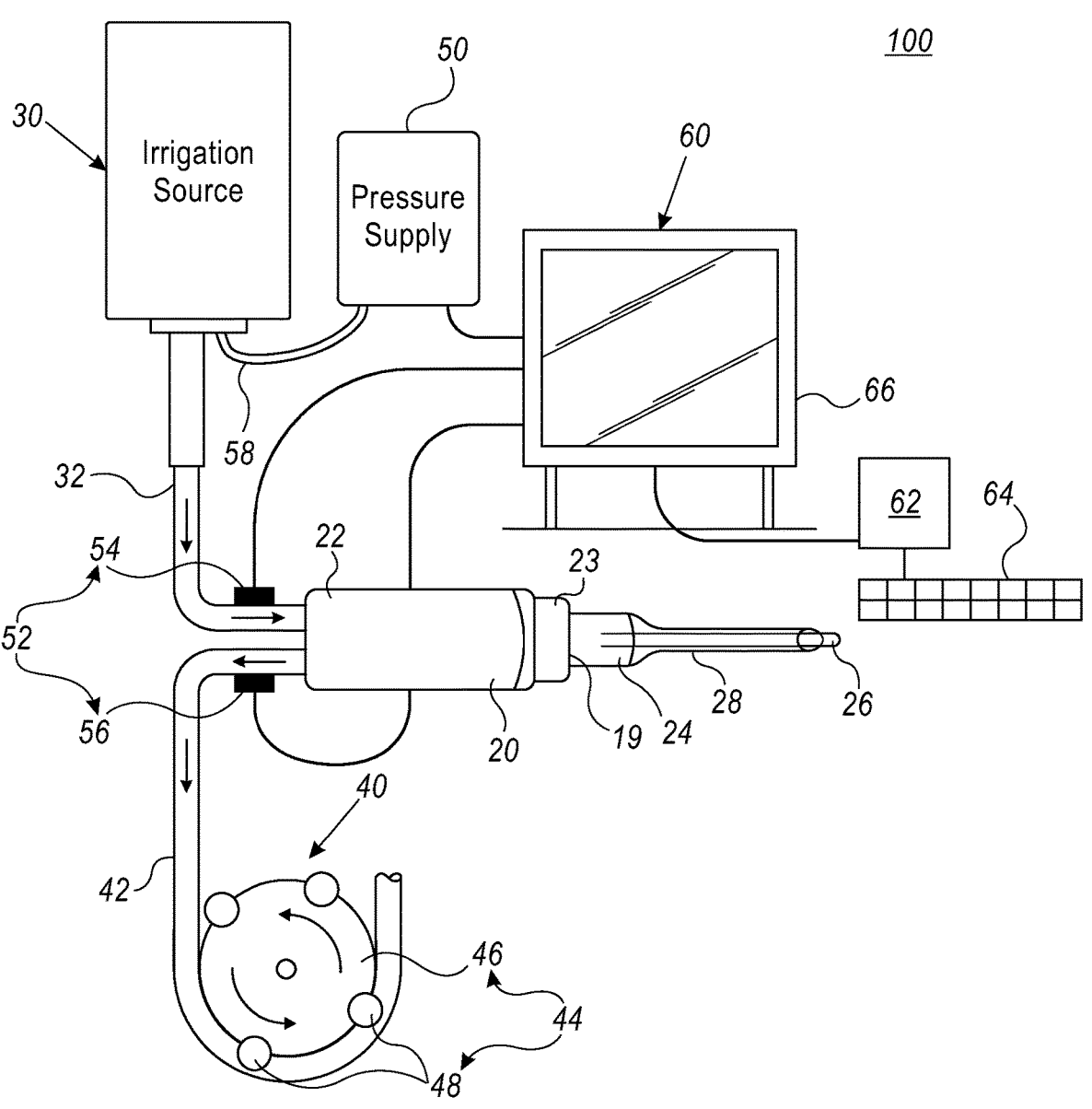
FIG. 1 is a diagram of an ophthalmic surgical system in accordance with the present disclosure.

FIG. 1 illustrates an exemplary phacoemulsification/diathermy/vitrectomy system 100. As illustrated, the system 100 includes, for example, a handpiece or wand 20, a tip 24, at the distal end 23 of the handpiece 20, an irrigation source 30, an aspiration source 40, an optional pressure supply 50, and a control module 60. The tip 24 includes a needle 26 which extends through the lumen of a sleeve 28 to a point beyond the sleeve 28.

Fluid is controllably directed through the system 100 in order to irrigate a patient's eye, via the tip 24, during an ocular surgical procedure. For example, the irrigation source may be a bag or bottle; the aspiration source 40 may be, for example, a peristaltic pump, Venturi pump, a progressive cavity pump (PCP), a combination of the aforementioned pumps, and/or similar type pumps know in the art; and optional pressure supply 50 may be any source known in the art to supply pressure to irrigation source 30, e.g. various types of pumps, such as, but not limited to peristaltic, Venturi, PCP, pneumatic, or a combination thereof. At the tip 24, irrigation is provided to the eye through the sleeve 28 that at least partially surrounds the needle 26, while aspiration is through the lumen of needle 26.

As illustrated in FIG. 1, the irrigation source 30 is configured to supply a predetermined amount of fluid to the handpiece 20 for use during surgical operation. Specifically, fluid may flow from the irrigation source 30 to the handpiece via an irrigation line 32. The irrigation source 30 may be any type of irrigation source 30 that can create and control a constant fluid flow such that vacuum pressure may be determined in the fluid flow, as known in the art. In illustrative examples, the irrigation source 30 may be configured to be an elevated drip bag 34 that supplies a steady state of fluid to the irrigation line 32. The pressure supply 50 may be coupled to the irrigation source 30 in order to maintain a constant pressure in the irrigation source 30 as fluid exits the irrigation source 30, as is known in the industry. Other examples of a uniform irrigation source are well known in the art.

During the surgical procedure, it may be necessary to remove or aspirate fluid and other material from the eye. Accordingly, fluid may be aspirated from the eye via the handpiece 20 to flow through an aspiration line 42 via an aspiration source 40. The aspiration source 40 may be any type of aspiration source 40 that creates a constant fluid flow such that vacuum pressure may be determined in the fluid flow. In illustrative examples, the aspiration source 40 may be configured to be a flow-based pump 44 (such as a peristaltic or scroll pump, or a PCP pump). The aspiration source 40 may create an aspiration system to pump a uniform or predetermined amount of fluid and/or material out of the eye via the aspiration line 42.

The handpiece 20 includes a first (proximal) end 22 and a second (distal) end 23 that includes means for attaching the tip 24, which is interchangeable depending on the specifics of the procedure. The tip 24 includes one or more irrigation ports, via the sleeve 28, and an aspiration port at the distal end of needle 26. The sleeve 28 is fluidly coupled to the irrigation line 32 to receive fluid flow from the irrigation source 30, and the needle 26 is fluidly coupled to the aspiration line 42 to receive fluid and/or material flow from the eye.

The handpiece 20 and the tip 24, for example, via the needle 26, may further emit ultrasonic energy into the patient's eye, for instance, to emulsify or break apart the crystalline lens within the patient's eye. Such emulsification may be accomplished by any known methods in the industry, such as, for example, a vibrating unit (not shown) that is configured to ultrasonically vibrate and/or cut the lens, as is known in the art. Other forms of emulsification, such as a laser, are well known in the art. Concomitantly with the emulsification, fluid from the irrigation source 30 is irrigated into the eye via the irrigation line 32 and sleeve 28. During and after such emulsification, the irrigation fluid and emulsified crystalline lens material are aspirated from the eye by the aspiration source 40 via the needle 26 and the aspiration line 42. Other medical techniques for removing crystalline lenses also typically include irrigating the eye and aspirating lens parts and other liquids.

The interchangeable tip 24 may be a predetermined or uniform shape and size, and typically further include various features that are beneficial to performing the surgical operation, such as various needle gauges, e.g., 19 gauge, 20 gauge and 21 gauge, the gap between the sleeve 28 inner diameter and outer diameter, needle 26 bevel, a bend in the tip and the degree of the bend, tip flare (the inner and outer diameter increase from the shaft to the end of the tip 24, and combinations thereof. Such tips 24 are generally known to be of uniform sizes or types in the industry, such that certain tips 24 may be considered advantageous for certain surgical maneuvers or operations. Tips of uniform size or type may be identified by specific name or product number to be an industry standard design. Surgeons or other users of such tips may have industry knowledge of the types of tips available and their varying characteristics, and may rely on the uniformity of tip types from operation to operation. It is extremely important to correctly identify the tip being used by its type, in order that the system 100 which the handpiece 20 and tip 24 are used function properly as part of the system 100.

A sensor system 52 determines input (irrigation) pressure, of fluid flowing through the sleeve 28 (sensor 54), and output (aspiration) pressure, flowing through the needle 26 (sensor 56).

The sensor system 52 may be configured in a variety of ways or located in various locations. For example, the sensor system 52 may include at least a first sensor or strain gauge 54, for measuring irrigation pressure, and a second sensor or strain gauge 56, for measuring aspiration pressure. At a point prior to the fluid flowing through the irrigation sleeve 28, the first sensor 54, such as a vacuum sensor or pressure transducer, is utilized to detect a variety of variables, such as fluid pressure or vacuum level, of fluid flowing into the eye. At a point after the fluid and materials flow through the aspiration needle 26, the second sensor 56, which may also be a vacuum sensor or pressure transducer, may be utilized to detect similar variables of the fluid flowing out of the eye via the needle 26 of handpiece 20. Other locations for the sensors 54 and 56 are envisioned anywhere along the irrigation line 32 and the aspiration line 42, respectively. In some examples, multiple sensors may be used on the aspiration line 42, tip 24 (irrigation and aspiration lines), and/or handpiece, and/or the irrigation line 32.

The system 100, for example, includes a control module 60 configured to monitor and control various components of the system 100. For instance, the control module 60 may monitor, control, and provide power to the pressure supply 50, the aspiration source 40, and/or the handpiece 20. The control module 60 may be in a variety of forms as known in the art. In illustrative example, the control module 60 may include a microprocessor computer 62, a keyboard 64 (which may be virtual displayed on a screen), and a display or screen 66. The microprocessor computer 62 may be operably connected to and control the various other elements of the system, while the keyboard 64 and display 66 permit a user to interact with and control the system components as well.

The microprocessor computer 62, for example, comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

For example, the control module 60 may also include a pulsed ultrasonic power source (not shown) that can be controlled by the computer 62 in accordance with known methods or algorithms in the art. A system bus (not shown) may be further provided to enable the various elements to be operable in communication with each other.

The screen 66 may display various measurements, criteria or settings of the system 100—such as the type of procedure, the phase of the procedure and duration of the phase, flow rate, the input and output pressures, and the tip 24 the system has been calibrated for. The screen 66 may be in the form of a graphical user interface (GUI) (not shown) associated with the control module 60, for tip selection and settings for particular tips, and utilizing a touchscreen interface, for example. The GUI may allow a user to monitor the characteristics of the system 100 and/or select settings or criteria for various components of the system. For instance, the GUI may permit a user to select or alter the maximum pressure being supplied by the pressure supply 50 to the irrigation source 30. The user may further control the operation of the phase of the procedure, the units of measurement used by the system 100, the height of the irrigation source 30, if applicable.

In one example, the pressure reading P may be indicative of the total pressure of the irrigation line 32, and may combine measurements of both the irrigation source height and the pressure provided into the pressure supply line 58. In this way, for example, the GUI may provide both an actual pressure reading based on direct measurement of the irrigation line 32, and a target or desired pressure based on the height of the irrigation source 30 and the pressure provided in the pressure supply line 58, if any. The GUI may further allow for the calibration and priming of the pressure in the irrigation source 30, as well as tuning with resonant frequencies. The GUI may also provide other options for the user, such as, for example, allowing for cancelling priming and tuning by selecting a button (or text box on a screen or touch screen).

Figure 2:
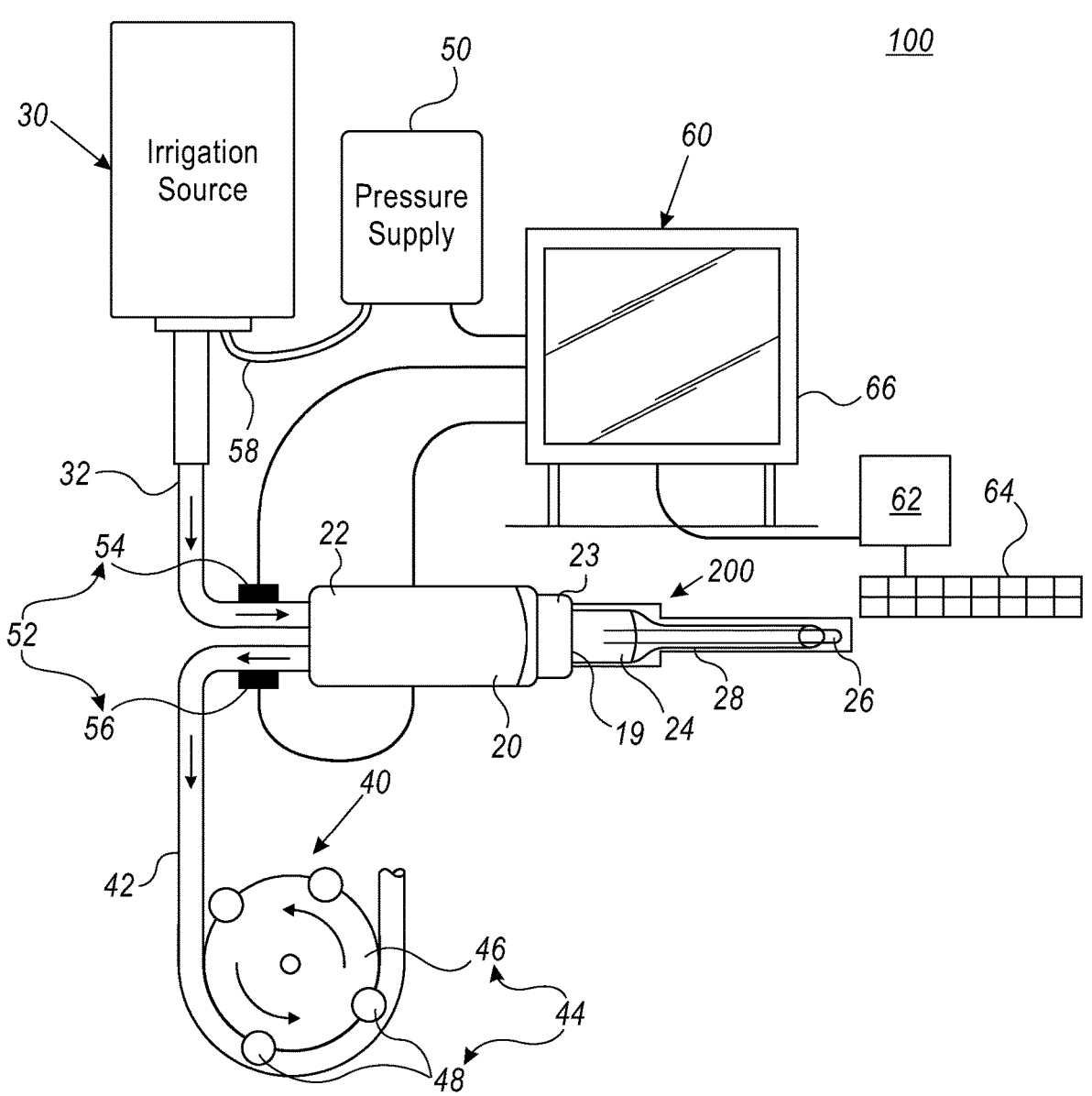
FIG. 2 is a diagram of the tip of the handpiece of the disclosed system in a calibration procedure.

FIG. 2 shows an exemplary phacoemulsification/dia-thermy/vitrectomy system 100 as shown in FIG. 1, but with a calibration chamber 200 placed over the tip 24, so as to seal the tip 24 from the ambient environment, in an air and fluid-tight manner. The calibration chamber 200 is, for example, of an elastomeric material with an interior for fitting over a tip 24, and typically corresponding in shape and dimensions to the exterior of the tip 24. The calibration chamber 200 is designed to sit flush against the distal end 23 of the handpiece 20, to seal the tip 24 from the ambient environment in an air-tight and fluid tight seal.

Both the irrigation line 32 and the aspiration line 42, via the tip 24, are primed. With the calibration chamber 200 fitted and sealed over the tip 24, the irrigation 32 and aspiration 42 lines are concurrently operated at a same flow rate to flush out any air in the irrigation line 32 and the aspiration 42 line. Once the system 100 is primed, the physician may remove the calibration chamber 200 and insert the tip 24 into the surgical site (the eye). The physician may switch between different tips during a procedure.

Figure 3A:
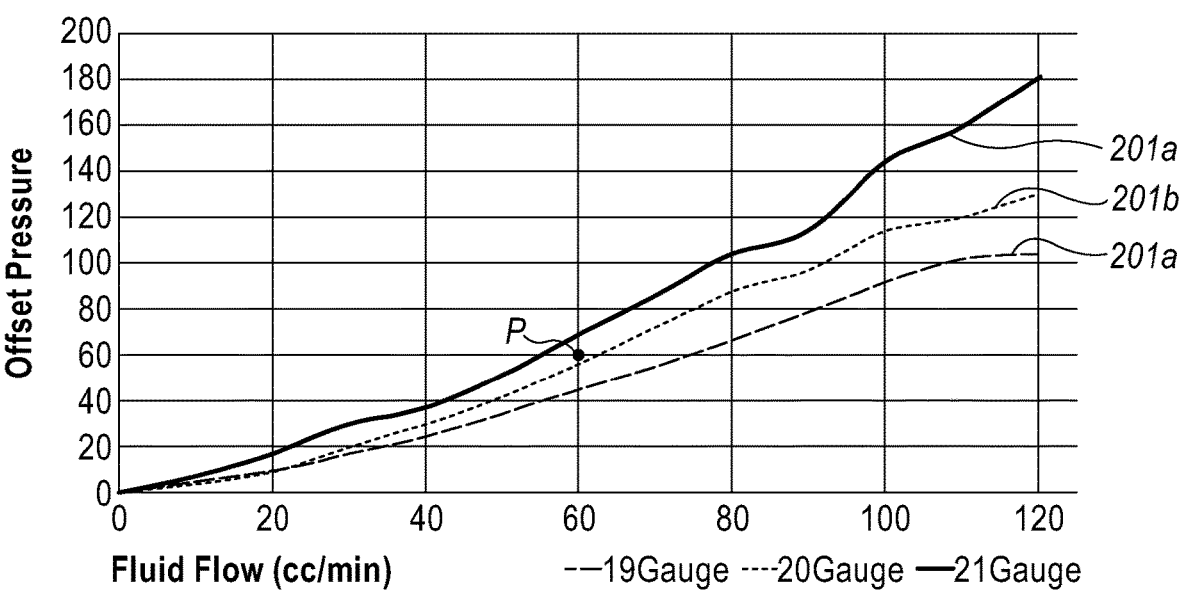
FIG. 3A is a diagram of offset pressures versus flow rates detected in an irrigation line of the disclosed system for tip types including a 19 gauge needle, a 20 gauge needle, and a 21 gauge needle.
Figure 3B:
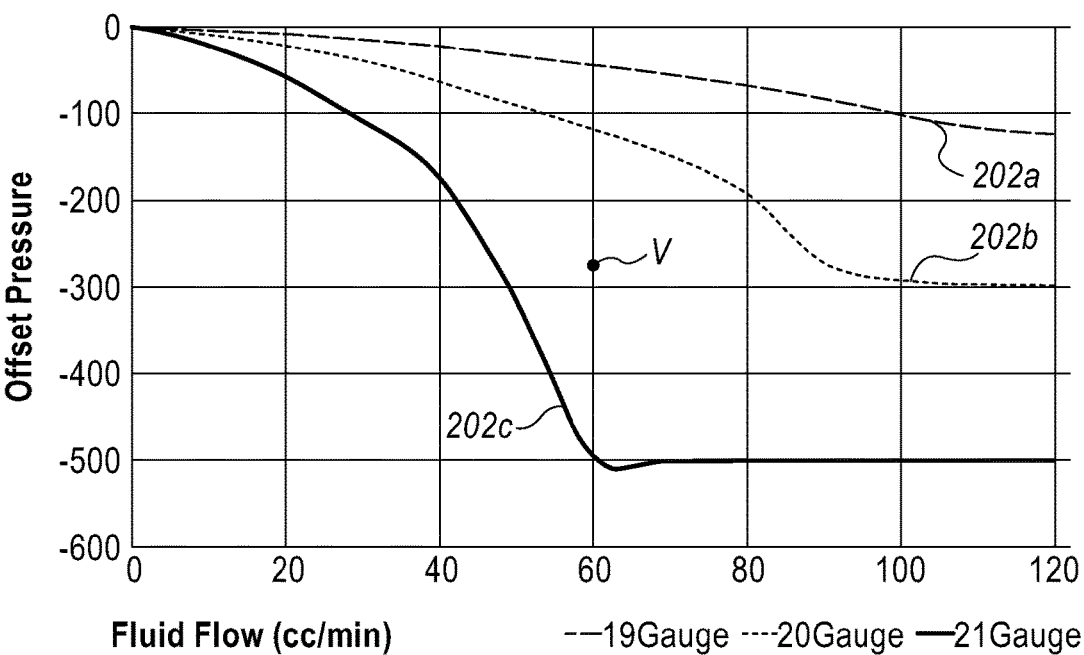
FIG. 3B is a diagram of offset pressures versus flow rates detected in an aspiration line of the disclosed system for tip types including a 19 gauge needle, a 20 gauge needle, and a 21 gauge needle.

For example, during the calibration, one or more pressures are detected by the respective sensors 54, 56, for example, in FIGS. 3A and 3B, at various flow rates, but operating at the same flow rate for irrigation and aspiration. The pressures, also known as offset pressures, at the same flow rates, for irrigation and aspiration, are recorded as data points for curves, for irrigation flows and pressures of FIG. 3A, and aspiration flows and pressures of FIG. 3B, obtained for each of the tips, e.g., 19 Gauge needle 201a (FIG. 3A) and 202a (FIG. 3B), 20 gauge needle 201b and 202b, and 21 gauge needle 201c and 202c. These values are used to create a look up table (LUT) between the difference or delta (Δ) between pressure of the irrigation line 32 and pressure of the aspiration line 42 for each flow rate, for each individual tip 24. The LUT is stored in the computer 62. Based on the diagrams of FIGS. 3A and 3B, the flow rate used in calibration and the difference (Δ) between offset pressures in irrigation and aspiration in the tip 24 is used to determine the tip type.

When deciding what flow rate is to be used during a calibration procedure, to determine tip type, the offset pressure should not be at a plateau. In a plateau, for example, in FIG. 3B, aspiration flow rates exceeding 60 cc/minute, result in pressure plateaus, meaning that even if aspiration flow rate is increased, pressure remains the same, such that calibrating at aspiration at flow rates above 60 cc/min will likely lead to an inaccurate result.

System Operation

In an example operation, performed by processors in the microprocessor computer 62, tip type is determined, which is shown by the flow diagram of FIG. 4A. The process begins at a START block 300, where a calibration procedure or priming of the tip 24 is set up, with the calibration chamber 200 attached to the handpiece 20, sealing the tip 24, as shown in FIG. 2. While priming the tip 24 during the calibration procedure by providing the same flow rate to the irrigation line 32 and the aspiration line 42 at block 302, pressure, as detected by the respective sensors 54, 56, is recorded along the irrigation 32 and aspiration 42 lines, at block 304. For example, the tip 24 is primed at a flow rate of, for example 20 cc/min to 60 cc/minute. As shown in FIG. 3B, 60 cc/min is selected, for it is not where offset pressure plateaus. Other flow rates may be selected, provided there is not a plateau for any of the flow rates for the tested tip types which make up the calibration charts (e.g., FIG. 3B, anywhere between 20 cc/min and 60 cc/min).

The recorded pressures, from the irrigation 32 and aspiration lines 42 at the flow rate of 60 cc/minute, are used to identify the tip 24 type, for example, a tip with a 19 gauge needle, a tip with a 20 gauge needle, or a tip with a 21 gauge needle, which is attached to the hand piece 20. For example, in FIG. 3A, for the irrigation line 32, the offset pressure detected by the sensor 54, for the flow rate of 60 cc/minute, is indicated by P. Similarly, in FIG. 3B, for the aspiration line 42, the offset pressure detected by the sensor 56, for the flow rate of 60 cc/minute, is indicated by V. A difference between the pressure readings on the irrigation 32 and aspiration 42 lines, for the calibration flow rate of 60 cc/minute, or delta (Δ) is calculated, at block 306. The calculation is based on offset pressure recorded on the aspiration line 42 minus offset pressure recorded on the irrigation line 32, at a flow rate of 60 cc/minute on both the aspiration 42 and irrigation 32 lines. The calculated delta (Δ) is compared to values on a LUT, at block 308, that is stored in computer 62 memory 66, to determine the tip type, at block 310.

It is important to specifically use the difference delta (Δ) between the pressure readings on the irrigation 32 and aspiration 42 lines, because the actual pressure in the calibration chamber 200 is unknown. Pressure in the calibration chamber 200 is sensitive to tolerances in the controlled flow parameters. Small differences in flow rate between the irrigation line 32 and the aspiration line 42, that are within tolerances, may lead to variability in the pressure of the calibration chamber 200. The tolerances are more of an issue in a progressive cavity pump (PCP) which may be used in the system 100, instead of peristaltic pumps.

Mathematically, the calculation for the delta (Δ) is, for example, as follows:

$$P=IOP+Poffset \tag{Equation 1}$$

In Equation 1, the value P is the pressure sensed (by the sensor 54) on the irrigation line 32 which will equal the pressure in the calibration chamber 200 (IOP)plus (+) a delta pressure (Poffset) related to sensing at a distance from the distal tip of the needle (see P in FIG. 3A).

$$V=IOP+Voffset \tag{Equation 2}$$

In Equation 2, the value V is the pressure sensed (by the sensor 56) on the aspiration line 42 which will equal the pressure in the calibration chamber 200 (IOP) plus (+) a delta pressure (Voffset) related to sensing at a distance from the distal tip of the needle (see V in FIG. 3B).

P and V will typically not fall on any of the calibration graphs due to the tolerances in the flow system. The tolerances are mostly due to the tolerances in the PCP. For this reason, it will be difficult to identify the tip by inspecting V and P individually.

Since IOP is equal for P and V, it can be eliminated, whereby:

$$V-P=Voffset-Poffset=Δ \tag{Equation 3}$$

In Equation 3, the A is a value used to identify the tip type by comparing it to A values in the LUT, for each of the possible tip types of the LUT.

With the tip 24 type determined, at block 310, verification of the tip type is performed during priming, by an example process of FIG. 4B. At the START block 350, the tip type is that determined at block 310.

Moving to block 352, the computer 62 determines whether the tip type determined is a tip type other than the tip selected by the physician (the physician selected tip is based on system settings, e.g., working parameters for various surgical procedures for which specific tips are used). If yes, the process moves to block 354, where the system 100 provides a warning to the physician and an indication that the system 100 will operate at system settings according to the tip type determined (identified) during the calibration (priming), at block 356. Returning to block 352, should the detected tip type match the tip type selected by the physician (based on system settings), the system settings for the system 100 are set to match the tip being used, i.e., the detected tip type, at block 358. Alternately, the system 100 can recognize the tip type and adjust system settings, on cases where the physician has not selected a tip type and accordingly, has not provided system settings.

In another example operation, tip type may be detected based on its resonant frequency in response to ultrasound transducer activation. The resonant frequency is periodically detected to determine whether the resonant frequency has changed. If there is a significant change in the resonant frequency, an alert is issued, typically in the form of a warning to the user (operator of the system 100). Based on the current resonant frequency, the tip type is determined (identified), and the system 100 is updated.

Figure 5:
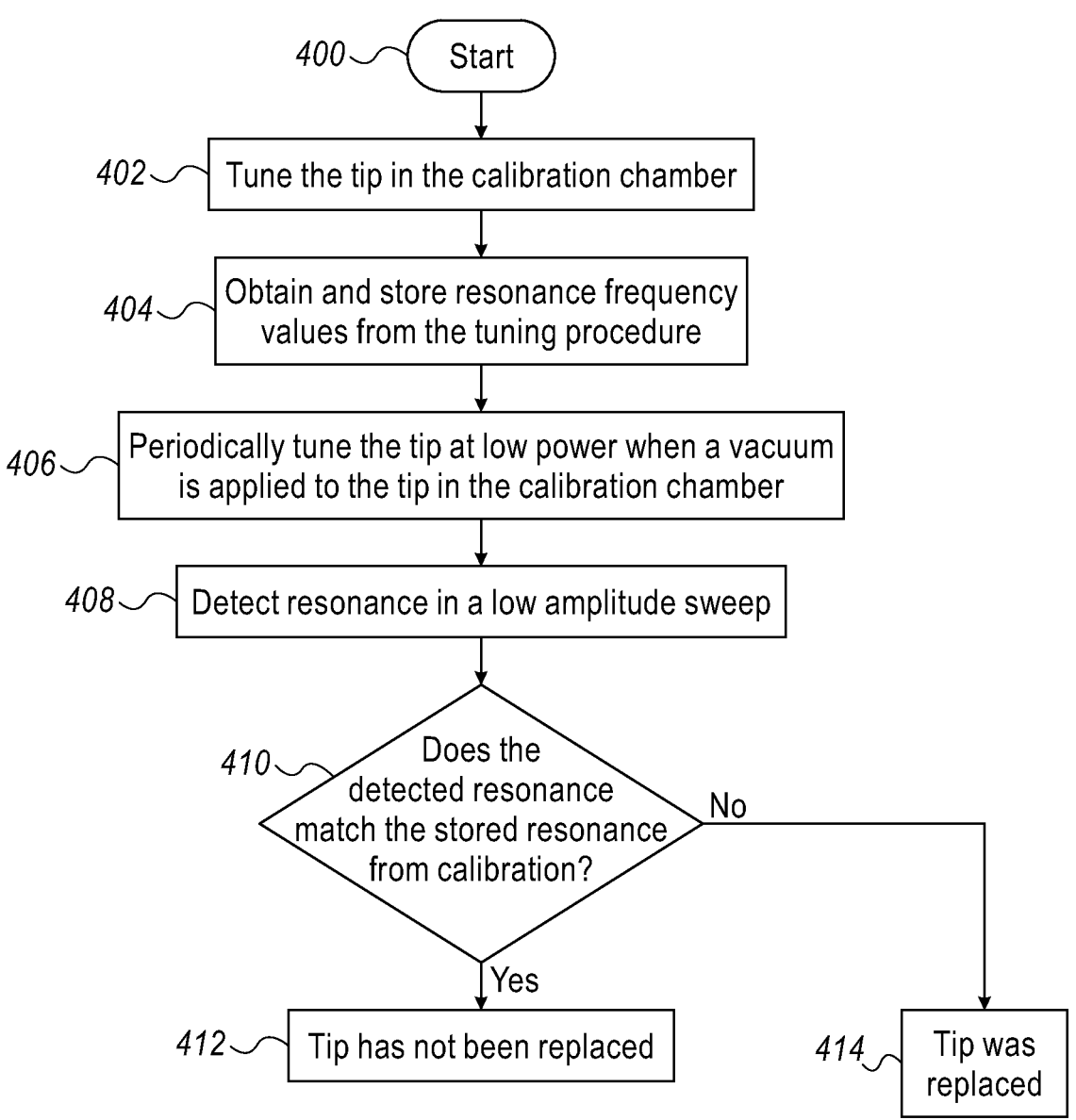
FIG. 5 is a flow diagram of an example process for determining tip type based on resonance frequency.

FIG. 5 is a flow diagram of a computerized process for detecting the tip type based on detected resonance frequency. The process is performed by processors in the microprocessor computer 62.

The process begins at a START block 400, where the tip 24 is calibrated, as detailed above. The calibration analyzes resonance frequencies of the needle 26, which is vibrated by an ultrasonic transducer within the handpiece 20. The ultrasonic transducer, for example, includes one or more piezoelectric crystals, to transfer vibrational energy to the needle 26 of the tip 24. The needle vibrations are driven by an electrical signal applied to the transducer, the frequency of the electrical signal determining the vibration frequency of the needle 26.

Moving to block 402, the tip 24 is tuned in the calibration chamber 200, as the ultrasound transducer sweeps over a range of frequencies for vibrating the needle 26, and detects resonance frequencies. The resonance frequency values are stored at block 404.

At block 406, when a vacuum is applied in the calibration chamber 200, periodically tuning is performed using a very low power signal (e.g., 100 mW to 1 Watt) from the transducer. At block 408, a low amplitude ultrasound sweep signal is superimposed over the actuating ultrasound signal for operating the handpiece 20 to perform phacoemulsification.

Figure 6:
FIG. 6 is a diagram of resonance frequencies obtained during detection of a tip type on a handpiece, in accordance with the present disclosure.

Based on this low amplitude sweep, the magnitude of the mechanical vibrations of the needle 26 of the tip 24, as a function of the frequency is detected and measured. The magnitude is maximal (maximal amplitude of vibrations for the needle 26) at the resonance frequency. For example, the resonance frequency is shown by the apex in FIG. 6, a graph of vibration amplitude (y-axis) versus time (x-axis), for a 19 Gauge needle and corresponding sleeve tip type.

Moving to block 410, if the resonance frequency matches the resonance frequency stored during calibration with the calibration chamber, it may be concluded that the tip has not been replaced, at block 412. If there is a significant change, this may be an indication that the tip 24 has been replaced, or the tip has been installed incorrectly on the handpiece 20, at block 414. For example, a significant change occurs when the correlation coefficient is less than 0.8.

Should there be a significant change, as indicated by the correlation coefficient being less than 0.8, the system 100 may issue a warning, including a warning to the surgeon.

Alternately, resonance frequencies for various tip types may be stored by the system in a Look Up Table (LUT), such that tip type detection occurs without input from the surgeon.

Those of skill in the art will recognize that any step of a method described in connection with an example may be interchanged with another step without departing from the scope of the invention. Those of skill in the art would further appreciate that the various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the examples disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

EXAMPLES

Example 1

A method for detecting the tip type for the tip (24) of a handpiece (20) of an ophthalmic instrument. The method comprises: placing a calibration chamber (200) over the tip (24) of the handpiece; priming the tip (24) by irrigating the tip (24) and aspirating the tip (24); measuring the irrigation pressure and the aspiration pressure during the priming of the tip (24); and, by a processor (62): calculating a value corresponding to the difference between the aspiration pressure and the irrigation pressure; and, analyzing the calculated value against one or more predetermined values for tip types, to determine the tip type.

Example 2

The method according to Example 1, wherein should the determined tip type be different than the tip (24) selected by the operator of the ophthalmic instrument, issue a warning to the operator.

Example 3

The method according to Example 1 or Example 2, wherein the one or more predetermined values for tip types are stored in a look up table (LUT).

Example 4

The method according to any of Example 1 to Example 3, wherein the analyzing the calculated value against one or more predetermined values for tip types comprises: comparing the calculated value against the one or more values of the LUT.

Example 5

The method according to any of Example 1 to Example 4, wherein the flow rate is approximately 60 cc/minute.

Example 6

The method according to any of Example 1 to Example 5, wherein the placing the calibration chamber (200) over the tip (24) includes sealing the tip (24) from the ambient environment.

Example 7

The method according to any of Example 1 to Example 6, wherein the irrigating the tip (24) and aspirating the tip (24) is at the same flow rate.

Example 8

The method according to any of Example 1 to Example 7, wherein the tip (24) includes a needle (26) of a dimension including one of: 19 gauge, 20 gauge or 21 gauge.

Example 9

The method according to any of Example 1 to Example 8, wherein the tip (24) comprises a sleeve (28) and a needle (26) extending therethrough.

Example 10

A method for detecting the tip type for the tip (24) of a handpiece (20) of an ophthalmic instrument. The method comprises: estimating the resonance frequency of a needle (26) in the tip (24) of the handpiece (20); and, identifying the type of the tip (24) based on the estimated resonance frequency of the needle (26).

Example 11

The method according to Example 10, wherein the estimating the resonance frequency comprises sweeping the frequency over a frequency range and determining the frequency for which the vibration amplitude for the needle (26) is maximal.

Example 12

The method according to Example 10 or Example 11, wherein the identifying the type of the tip (24) comprises analyzing the frequency determined for which the vibration amplitude for the needle (26) is maximal against predetermined resonance frequencies for one or more types of tips (24) of handpieces (20).

Example 13

The method according to any of Example 10 to Example 12, wherein the estimating the resonance frequency is performed during calibration of the tip (24).

Example 14

The method according to any of Example 10 to Example 13, wherein the tip (24) comprises a sleeve (28) and a needle (26) extending therethrough.

Example 15

A system (100) for detecting the tip type for the tip (24) of a handpiece (20) of an ophthalmic instrument. The system (100) comprises: at least one first sensor (54) in communication with an irrigation line (32) of the handpiece (20) for measuring irrigation pressure in the irrigation line during priming of the tip (24) of the handpiece (20); at least one second sensor (56) in communication with an aspiration line (42) of the handpiece (24) for measuring aspiration pressure in the aspiration line (42) during priming of the tip (24) of the handpiece (20); and, a processor (62) in communication with the at least one first sensor (54) and the at least one second sensor (56), the processor (62) programmed to: calculate a value corresponding to the difference between the aspiration pressure and the irrigation pressure; and, analyze the calculated value against one or more predetermined values for tip types, to determine the tip type.

Example 16

The system (100) according to Example 15, wherein the processor (62) is additionally programmed to: issue a warning to an operator of the system (100), should the determined tip type be different than the tip (24) selected by an operator of the ophthalmic instrument.

Example 17

The system (100) according to Example 15 or Example 16, additionally comprising: a storage media in communication with the processor (62) for storing one or more predetermined values for tip types as a look up table (LUT).

Example 18

The system according to any one of Example 15 to Example 17, wherein the processor (62) is further programmed to analyze the calculated value against one or more predetermined values for tip types by comparing the calculated value against the one or more values of the LUT.

Example 19

A system for detecting the tip type for the tip (24) of a handpiece (20) of an ophthalmic instrument. The system (100) comprises: an ultrasonic transducer in the handpiece (20) for vibrating a needle (26) in the tip (24); and, a processor (62) programmed to: cause the ultrasonic transducer to vibrate the needle (26) at an estimated resonance frequency of the needle (26); and, identify the type of the tip (24) based on the estimated resonance frequency of the needle (26).

Although the examples disclosed herein mainly address phacoemulsification procedures, the methods and systems disclosed herein can also be used in other applications, such as in vitrectomy surgery and other ophthalmic surgical procedures.

It will thus be appreciated that the examples described above are not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for detecting the tip type for the tip of a handpiece of an ophthalmic instrument comprising:
   placing a calibration chamber over the tip of the handpiece;
   priming the tip by irrigating the tip and aspirating the tip;
   measuring the irrigation pressure and the aspiration pressure during the priming of the tip; and
   by a processor:
      calculating a value corresponding to the difference between the aspiration pressure and the irrigation pressure; and
      analyzing the calculated value against one or more predetermined values for tip types, to determine the tip type.

2. The method of claim 1, wherein should the determined tip type be different than the tip selected by the operator of the ophthalmic instrument, issue a warning to the operator.

3. The method of claim 1, wherein the one or more predetermined values for tip types are stored in a look up table (LUT).

4. The method of claim 3, wherein the analyzing the calculated value against one or more predetermined values for tip types comprises: comparing the calculated value against the one or more values of the LUT.

5. The method of claim 1, wherein the flow rate is approximately 60 cc/minute.

6. The method of claim 1, wherein the placing the calibration chamber over the tip includes sealing the tip from the ambient environment.

7. The method of claim 1, wherein the irrigating the tip and aspirating the tip is at the same flow rate.

8. The method of claim 1, wherein the tip includes a needle of a dimension including one of: 19 gauge, 20 gauge or 21 gauge.

9. The method of claim 1, wherein the tip comprises a sleeve and a needle extending therethrough.

10. A method for detecting the tip type for the tip of a handpiece of an ophthalmic instrument comprising:

estimating the resonance frequency of a needle in the tip of the handpiece; and
identifying the type of the tip based on the estimated resonance frequency of the needle.

11. The method of claim 10, wherein the estimating the resonance frequency comprises sweeping the frequency over a frequency range and determining the frequency for which the vibration amplitude for the needle is maximal.

12. The method of claim 11, wherein the identifying the type of the tip comprises analyzing the frequency determined for which the vibration amplitude for the needle is maximal against predetermined resonance frequencies for one or more types of tips of handpieces.

13. The method of claim 10, wherein the estimating the resonance frequency is performed during calibration of the tip.

14. The method of claim 10, wherein the tip comprises a sleeve and a needle extending therethrough.

15. A system for detecting the tip type for the tip of a handpiece of an ophthalmic instrument comprising:
   at least one first sensor in communication with an irrigation line of the handpiece for measuring irrigation pressure in the irrigation line during priming of the tip of the handpiece;
   at least one second sensor in communication with an aspiration line of the handpiece for measuring aspiration pressure in the aspiration line during priming of the tip of the handpiece; and
   a processor in communication with the at least one first sensor and the at least one second sensor, the processor programmed to:
      calculate a value corresponding to the difference between the aspiration pressure and the irrigation pressure; and
      analyze the calculated value against one or more predetermined values for tip types, to determine the tip type.

16. The system of claim 15, wherein the processor is additionally programmed to: issue a warning to an operator of the system, should the determined tip type be different than the tip selected by an operator of the ophthalmic instrument.

17. The system of claim 16, additionally comprising: a storage media in communication with the processor for storing one or more predetermined values for tip types as a look up table (LUT).

18. The system of claim 17, wherein the processor is further programmed to analyze the calculated value against one or more predetermined values for tip types by comparing the calculated value against the one or more values of the LUT.

19. A system for detecting the tip type for the tip of a handpiece of an ophthalmic instrument comprising:
   an ultrasonic transducer in the handpiece for vibrating a needle in the tip; and
   a processor programmed to:
      cause the ultrasonic transducer to vibrate the needle at an estimated resonance frequency of the needle; and
      identify the type of the tip based on the estimated resonance frequency of the needle.

* * * * *